(12) United States Patent
Waldo

(10) Patent No.: US 6,448,087 B1
(45) Date of Patent: Sep. 10, 2002

(54) METHOD FOR DETERMINING AND MODIFYING PROTEIN/PEPTIDE SOLUBILITY

(75) Inventor: Geoffrey S. Waldo, Espanola, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/410,889

(22) Filed: Sep. 30, 1999

Related U.S. Application Data

(63) Continuation-in-part of application No. 08/989,380, filed on Dec. 12, 1997, now abandoned.

(51) Int. Cl.[7] .......................... G01N 33/00; C12Q 1/02; C12P 21/06; C12P 21/04; C12N 1/21

(52) U.S. Cl. .......................... 436/86; 435/29; 435/69.1; 435/69.7; 435/252.3; 435/320.1; 435/325; 536/23.4; 436/2

(58) Field of Search .......................... 435/4, 7.1, 7.9, 435/29, 69.1, 69.7, 252.3, 320.1, 325; 436/23.4, 86, 2

(56) References Cited

U.S. PATENT DOCUMENTS 5,491,084 A  2/1996  Chalfie et al. .............. 435/189

OTHER PUBLICATIONS

Maxwell, K., et al., Protein Science, vol. 8, 1999, pp. 1908–1911.*
Willem P.C. Stemmer, "Rapid Evolution Of A Protein In Vitro By DNA Shuffling," Nature 370, 389 (1994).
Willem P.C. Stemmer, "DAN Shuffling By Random Fragmentation And Reassembly: In Vitro Recombination For Molecular Evolution," Proc. Natl. Acad. Sci. USA 91, 10747 (1994).
Willem P.C. Stemmer, "Searching Sequence Space: Using Recombination to Search More Efficiently and Thoroughly Instead of Making Bigger Combinatorial Libraries," Biotechnology 13, 549 (1995).
Frances H. Arnold, "Directed Evolution: Creating Biocatalysts for the Future," Chemical Engineering Science 51, 5091 (1996).
Ji–Hu Zhang et al., "Directed Evolution Of A Fucosidase from a Galactosidase by DNA Shuffling and Screening," Proc. Natl. Acad. Sci. USA 94, 4504 (1997).
Huimin Zhao et al., "Functional and Nonfunctional Mutations Distinguished by Random Recombination of Homologous Genes," Proc. Natl. Acad. Sci. USA 94, 99 (1997).
Jeffrey C. Moore et al., "Strategies for the In Vitro Evolution of Protein Function: Enzyme Evolution by Random Recombination of Improved Sequences", J. Mol. Biol. 272, 336 (1997).
Andreas Crameri et al., "Improved Green Fluorescent Protein by Molecular Evolution Using DNA Shuffling," Nature Biotechnology 14, 315 (1996).
Roger Heim et al., "Wavelength Mutations and Posttranslational Autoxidation of Green Fluorescent Protein," Proc. Natl. Acad. Sci. USA 91, 12501 (1994).
Chun Wu et al., "Novel Green Fluorescent Protein (GFP) Baculovirus Expression Vectors," Gene 190, 157 (1997).
N. Garamszagi et al., "Application of a Chimeric Green Fluorescent Protein to Study Protein–Protein Interactions," Biotechniques 23, 864 (1997).
G. MacBeath, et al., "Redesigning Enzyme Topology by Directed Evolution," Science 279, 1958 (1998).
Pierre Martineau et al., "Expression of an Antibody Fragment at High Levels in the Bacterial Cytoplasm," J. Mol. Biol. 280, 117 (1998).
Karl Proba et al., "Antibody scFv Fragments Without Disulfide Bonds Made by Molecular Evolution," J. Mol. Biol. 275, 245 (1998).
Zhanglin Lin et al., "Functional Expression of Horseradish Peroxidase in E. coli by Directed Evolution," Biotechnol. Prog. 15, 467 (1999).
Geoffrey S. Waldo et al., "Rapid Protein–Folding Assay Using Green Fluorescent Protein" Nature Biotechnology 17, 691 (1999).
Russell Higuchi, "Recombinant PCR" in "PCR Protocols, a Guide to Methods and Applications", Michael A. Innis, David H. Gelfand, John J. Sninsky, and Thomas J. White, eds. Academic press, Inc., 177 (1990).
Roger Helm et al., "Improved Green Fluorescence," Nature 373, 663 (1995).
Sorel Fitz–Gibbon et al. "A Fosmid–based Genomic Map and Identification of 474 Genes of the Hyperthermophilic Archaeon *Pyrobaculum aerophilum*." Extremophiles 1, 36 (1997).
Geoffrey Zubay, "In Vitro Synthesis of Protein in Microbial Systems." Ann. Rev. Genet. 7, 267 (1973).

(List continued on next page.)

*Primary Examiner*—Rebecca E. Prouty
*Assistant Examiner*—Delia Ramirez
(74) *Attorney, Agent, or Firm*—Samuel M. Freund

(57) ABSTRACT

A solubility reporter for measuring a protein's solubility in vivo or in vitro is described. The reporter, which can be used in a single living cell, gives a specific signal suitable for determining whether the cell bears a soluble version of the protein of interest. A pool of random mutants of an arbitrary protein, generated using error-prone in vitro recombination, may also be screened for more soluble versions using the reporter, and these versions may be recombined to yield variants having further-enhanced solubility. The method of the present invention includes "irrational" (random mutagenesis) methods, which do not require a priori knowledge of the three-dimensional structure of the protein of interest. Multiple sequences of mutation/genetic recombination and selection for improved solubility are demonstrated to yield versions of the protein which display enhanced solubility.

7 Claims, 5 Drawing Sheets

OTHER PUBLICATIONS

Frederick C. Neidhardt, "Chemical Composition of *Escherichia coli*," Neidhardt, F. C., ed. in *Escherichia coli* and *Salmonella typhimurium*: Cellular and Molecular Biology, pp. 3–6, American Society of Microbiology, Washington, D. C. (1987).

Yang Zhang et al., "Expression of Eukaryotic Proteins in Soluble Form in *Escherichia coli*", Protein Expr. Purif. 12, 159 (1998).

Frances H. Arnold, "Directed Evolution: Creating Biocatalysts for the Future." Chem. Eng. Sci. 51, 5091 (1996).

Humin Zhao et al., "Optimization of DNA Shuffling for High Fidelity Recombination." Nuc. Acids Res. 25, 1307 (1997).

Thomas C. Terwilliger et al., "In–vivo Characterization of Mutants of the Bacteriophage–f1 Gene V Protein Isolated by Saturation Mutagenesis." J. Mol. Biol. 236, 556 (1994).

Lynn F. Dickey et al. "Differences in the Regulation of Messenger–RNA for Housekeeping and Specialized–Cell Ferritin: A Comparison of Three Distinct Ferritin Complementary DNAs, the Corresponding Subunits, and Identification of the First Processed Pseudogene in Amphibia." J. Biol. Chem. 262, 7901 (1987).

Geoffrey S. Waldo et al., "Ferritin and Iron Biomineralization", Comprehensive Supramolecular Chemistry 5, pp. 65–91, Susslick, K. vol. ed., Pergamon Press, U.K., (1996).

Willem P. C. Stemmer, "Rapid Evolution of a Protein In–Vitro by DNA Shuffling." Nature 370, 389 (1994).

P. M. Harrison and P. Arosio, "The Ferritins: Molecular Properties, Iron Storage Function and Cellular Regulation." Biochim. et Biophys. Acta. 1275, 161 (1996).

T. Moos et al., "A Sensitive Post–DAB Enhancement Technique for Demonstration of Iron in the Central–Nervous System." Histochem. 99, 471 (1993).

Malcolm J. Casadaban et al., "β–Galactosidase Gene Fusions for Analyzing Gene Expression in *Escherichia coli* and Yeast," Methods Enzymol. 100, 293 (1983).

Maria T. Martin et al., "Determination of Polyprotein Processing Sites by Amino Terminal Sequencing of Nonstructural Proteins Encoded by Plum Pox Polyvirus", Virus Res. 15, 97 (1990).

Rolf Lutz et al., "Independent and Tight Regulation of Transcriptional Units in *E. coli* via the LacR/O, the TetR/O and AraD/$I_1$–$I_2$ Regulatory Elements", Nucleic Acids Res., 25(6), 1203 (1997).

* cited by examiner

Ferritin Variant

SEQUENCE LISTING

<160> NUMBER OF SEQ ID NOS: 5

<210> SEQ ID NO 1
<211> LENGTH: 24
<212> TYPE: DNA
<213> ORGANISM: Escherichia coli

<400> SEQUENCE: 1
catatgtgta gacagctggg atcc                                              24

<210> SEQ ID NO 2
<211> LENGTH: 36
<212> TYPE: DNA
<213> ORGANISM: Escherichia coli

<400> SEQUENCE: 2
ggatccgctg gctccgctgc tggttctggc gaattc                                 36

<210> SEQ ID NO 3
<211> LENGTH: 12
<212> TYPE: PRT
<213> ORGANISM: Escherichia coli

<400> SEQUENCE: 3

Gly Ser Ala Gly Ser Ala Ala Gly Ser Gly Glu Phe
1               5                   10

<210> SEQ ID NO 4
<211> LENGTH: 33
<212> TYPE: DNA
<213> ORGANISM: Escherichia coli

<400> SEQUENCE: 4
gatatagaat tcagcaaagg agaagaactt ttc                                    33

<210> SEQ ID NO 5
<211> LENGTH: 33
<212> TYPE: DNA
<213> ORGANISM: Escherichia coli

<400> SEQUENCE: 5
gaattcggta ccttatttgt agagctctac cat                                    33

METHOD FOR DETERMINING AND MODIFYING PROTEIN/PEPTIDE SOLUBILITY

CROSS-REFERENCE TO RELATED PATENT APPLICATIONS

The present patent application is a continuation-in-part of patent application Ser. No. 08/989,380 for "Method For Determining And Modifying Protein/Peptide Solubility" by Geoffrey S. Waldo which was filed on Dec. 12, 1997, now abandoned.

FIELD OF THE INVENTION

The present invention relates generally to improving the solubility of proteins/peptides and, more particularly to a method for identifying more or less soluble proteins/peptides from libraries of mutants thereof generated from the directed evolution of genes which express these proteins/peptides. This invention was made with government support under Contract No. W-7405-ENG-36 awarded by the U.S. Department of Energy to The Regents of the University of California. The government has certain rights in the invention.

BACKGROUND OF THE INVENTION

Protein insolubility constitutes a significant problem in basic and applied bioscience, in many situations limiting the rate of progress in these areas. Protein folding and solubility has been the subject of considerable theoretical and empirical research. However, there still exists no general method for improving intrinsic protein solubility. Such a method would greatly facilitate protein structure-function studies, drug design, de novo peptide and protein design and associated structure-function studies, industrial process optimization using bioreactors and microorganisms, and many disciplines in which a process or application depends on the ability to tailor or improve the solubility of proteins, screen or modify the solubility of large numbers of unique proteins about which little or no structure-function information is available, or adapt the solubility of proteins to new environments when the structure and function of the protein(s) are poorly understood or unknown.

Overexpression of cloned genes using an expression host, for example *E. coli*, is the principal method of obtaining proteins for most applications. Unfortunately, many such cloned foreign proteins are insoluble or unstable when overexpressed. There are two sets of approaches currently in use which deal with such insoluble proteins. One set of approaches modifies the environment of the protein in vivo and/or in vitro. For example, proteins may be expressed as fusions with more soluble proteins, or directed to specific cellular locations. Chaperons may be coexpressed to assist folding pathways. Insoluble proteins may be purified from inclusion bodies using denaturants and the protein subsequently refolded in the absence of the denaturant. Modified growth media and/or growth conditions can sometimes improve the folding and solubility of a foreign protein. However, these methods are frequently cumbersome, unreliable, ineffective, or lack generality. A second set of approaches changes the sequence of the expressed protein. Rational approaches employ site-directed mutation of key residues to improve protein stability and solubility. Alternatively, a smaller, more soluble fragment of the protein may be expressed. These approaches require a priori knowledge about the structure of the protein, knowledge which is generally unavailable when the protein is insoluble. Furthermore, rational design approaches are best applied when the problem involves only a small number of amino-acid changes. Finally, even when the structure is known, the changes required to improve solubility may be unclear. Thus, many thousands of possible combinations of mutations may have to be investigated leading to what is essentially an "irrational" or random mutagenesis approach. Such an approach requires a method for rapidly determining the solubility of each version.

Random or "irrational" mutagenesis redesign of protein solubility carries the possibility that the native function of the protein may be destroyed or modified by the inadvertent mutation of residues which are important for function, but not necessarily related to solubility. However, protein solubility is strongly influenced by interaction with the environment through surface amino acid residues, while catalytic activities and/or small substrate recognition often involve partially buried or cleft residues distant from the surface residues. Thus, in many situations, rational mutation of proteins has demonstrated that the solubility of a protein can be modified without destroying the native function of the protein. Modification of the function of a protein without effecting its solubility has also been frequently observed. Furthermore, spontaneous mutants of proteins bearing only 1 or 2 point mutations have been serendipitously isolated which have converted a previously insoluble protein into a soluble one. This suggests that the solubility of a protein can be optimized with a low level of mutation and that protein function can be maintained independently of enhancements or modifications to solubility. Furthermore, a screen for function may be applied concomitantly after each round of solubility selection during the directed evolution process.

In the absence of a screen for function, for example when the function is unknown, the final version of the protein can be backcrossed against the wild type in vitro to remove nonessential mutations. This approach has been successfully applied by Stemmer in "Rapid Evolution Of A Protein In Vitro By DNA Shuffling," by W. P. C. Stemmer, Nature 370, 389 (1994), and in "DNA Shuffling By Random Fragmentation And Reassembly: In Vitro Recombination For Molecular Evolution," by W. P. C. Stemmer, Proc. Natl. Acad. Sci. USA 91, 10747 (1994) to problems in which the function of a protein had been optimized and it was desired to remove nonessential mutations accumulated during directed evolution. The development of highly specialized protein variants by directed, in vitro evolution, which exerts unidirectional selection pressure on organisms, is further discussed in: "Searching Sequence Space: Using Recombination To Search More Efficiently And Thoroughly Instead Of Making Bigger Combinatorial Libraries," by Willem P. C. Stemmer, Biotechnology 13, 549 (1995); in "Directed Evolution: Creating Biocatalysts For The Future," by Frances H. Arnold, Chemical Engineering Science 51, 5091 (1996); in "Directed Evolution Of A Fucosidase From A Galactosidase By DNA Shuffling And Screening," by Ji-Hu Zhang et al., Proc. Natl. Acad. Sci. USA 94, 4504 (1997); in "Functional And Nonfunctional Mutations Distinguished By Random Combination Of Homologous Genes," by Huimin Zhao and Frances H. Arnold, Proc. Natl. Acad. Sci. USA 94, 7007 (1997); and in "Strategies For The In Vitro Evolution of Protein Function: Enzyme Evolution By Random Recombination of Improved Sequences", by Jeff Moore et al., J. Mol. Biol. 272, 336–346 (1997). Therein, efficient strategies for engineering new proteins by multiple generations of random mutagenesis and recombination coupled with screening for improved variants is described. However, there are no teachings concerning the use of directed evolutionary processes to improve solubility of proteins; rather, the mutagenesis was directed to improvement of protein function. It should be mentioned, however, that in order for the protein to function properly in any environment, it must at least be correctly folded.

Finally, for structural determination it is often not necessary or even desirable to have a fully functional version of the protein. If the mutational rate is low (ensured by molecular backcrossing), it is likely that the structure of the wild-type and solubility optimized versions of a protein will be similar. As long as the protein is soluble, and a structure can be obtained, it should then be possible to redesign the solubility of the protein using rational methods, if desired.

Green fluorescent protein has become a widely used reporter of gene expression and regulation. DNA shuffling has been used to obtain a mutant having a whole cell fluorescence 45-times greater than the standard, commercially available plasmid GFP.

See, e.g., "Improved Green Fluorescent Protein By Molecular Evolution Using DNA Shuffling," by Andreas Crameri et al., Nature Biotechnology 14, 315 (1996). The screening process optimizes the function of GFP (green fluorescence), and thus uses a functional screen. Although the screening process coincidentally optimizes the solubility of the GFP, in that the GFP is only fluorescent when properly folded, there is no mention of using soluble GFP as a tag to monitor solubility of other proteins; that is, the function of the protein and not its solubility are being modified. In "Wavelength Mutations And Post-translational Autooxidation Of Green Fluorescent Protein," by Roger Heim et al., Proc. Natl. Acad. Sci. USA 91, 12501 (1994), GFP was mutagenized and screened for variants with altered absorption or emission spectra. The authors mention that in place of proteins labeled with fluorescent tags to detect location and sometimes their conformational changes both in vitro and in intact cells, a possible strategy would be to concatenate the gene for the nonfluorescent protein of interest with the gene for a naturally fluorescent protein and express the fusion product. However, the focus of this paper is the extension of the usefulness of GFP by enabling visualization of differential gene expression and protein localization and measurement of protein association by fluorescence resonance energy transfer, by making available two visibly distinct colors. There is no mention of the use of the gene construct for solubility determinations. The paper further discusses the expression of GFP in *E. coli* under the control of a T7 promoter, and that the bacteria contained inclusion bodies consisting of protein indistinguishable from jellyfish or soluble recombinant protein on denaturing gels, but that this material was completely nonfluorescent, lacked the visible absorbance bands of the chromophore, and did not become fluorescent when solubilized and subjected to protocols that renature GFP, as opposed to the soluble GFP in the bacteria which undergoes correct folding and, therefore, fluoresces.

Chun Wu et al. in "Novel Green Fluorescent Protein (GFP) Baculovirus Expression Vectors," Gene 190, 157 (1997), describe the construction of Baculovirus expression vectors which contain GFP as a reporter gene. The authors follow the production and purification of a protein of interest by in-frame cloning of the gene that expresses the protein in insect cells with the GFP open reading frame, thereby permitting visualization of the produced GFP-fusion protein using UV light. However, the purified GFP-XylE fusion protein was found to be insoluble after harvest. The authors did not correlate the level of fluorescence of the cells expressing the GFP-XylE fusion protein with the solubility of cells expressing the XylE protein alone. Therefore, this reference does not teach the use of the fusion protein fluorescence as an indicator of the solubility of the specific protein XylE or of the solubility of other proteins.

In "Application Of A Chimeric Green Protein Fluorescent Protein To Study Protein-Protein Interactions," by N. Garamszegi et al., Biotechniques 23, 864 (1997), the authors discuss the fusion between GFP and human calmodulin-like protein (CLP) and show that this protein retains fluorescence and the known characteristics of CLP. That is, the GFP portion remains responsible for efficient fluorescent signals with little or no influence on the properties of the fused protein of interest. The authors maintain that the exhibited GFP fluorescence provides information concerning the maintenance of the GFP structural integrity in the chimeric protein, but does not provide information about the integrity of the entire fusion protein and, in particular, does not allow any statements concerning the maintenance of CLP function or integrity. From these statements, it is clear that this paper does not contemplate the use of the GFP as a solubility reporter for the CLP.

It has been demonstrated that improving the apparent functionality of a protein can sometimes increase the concomitant solubility of the protein, as in: "Redesigning enzyme topology by directed evolution," by G. Macbeath, P. Kast, and D Hilvert, Science 279, 1958–1961 (1998); "Expression of an antibody fragment at high levels in the bacterial cytoplasm," by P. Martineau, P. Jones, and G. Winter, J. Mol. Biol. 280, 117–127 (1998); "Antibody scFv fragments without disulfide bonds made by molecular evolution," K. Proba, A. Worn, A. Honegger, and A. Pluckthun, J. Mol. Biol. 275, 245–253 (1998); and "Functional Expression of Horseradish Peroxidase in *E. coli* by Directed Evolution," Lin Zhanglin, Todd Thorsen, and Frances H. Arnold, Biotechnol. Prog. 15, 467–471 (1999). In each case, the driving force for the directed evolution was the functionality of the protein of interest. For example, if the protein was an enzyme, the assay for improved function was the turnover of a chromogenic analog of the enzyme's natural substrate; if the protein was an antibody, it was the recognition of the target antigen by the antibody. For cytoplasmic expression of antibodies, the recognition was linked to cell survival, (binding of the antibody to a selectable protein marker which was an antigen for the antibody of interest providing selection for functional antibodies); in the case of phage displayed antibodies without disulfide bonds, the recognition was transduced to successful binding of the displayed phage to the target antigen of the displayed antibody in a biopanning protocol. The authors expressed the proteins in *E. coli*, and noted an apparent increase in the amount of protein expressed in the soluble fraction relative to the unselected target proteins, noting that the apparent increase in activity of desirable mutants during the evolution was due at least in part to an increase in the number of correctly folded (and hence functional) protein molecules, and not exclusively to an increase in the specific activity of a given protein molecule. However, the driving force for the selection or screening process during the directed evolution depended on the functionality (and functional assay for) the protein of interest. Many proteins have no easily detectable functional assay, and thus identification of proteins with improved folding yield by an increase in apparent activity due to a larger number of correctly folded molecules, is not a general method for improving folding by directed evolution. Furthermore, even when functional assays are available, apparent increases in activity can also be due to increases in the specific activity (activity of an individual protein molecule) even when the total number of correctly folded molecules remains the same. Thus, increases in apparent activity do not necessarily translate to increases in the solubility of proteins. Furthermore, functional assays are protein-specific, and thus must be developed on a case-by-case basis for each new protein. Functional assays therefore lack the generality needed to identify proteins which are soluble, or to find genetic variants (mutants and fragments) of proteins with improved solubility, in a high-throughput manner for proteomics or functional genomics wherein large numbers of different proteins about which little or no functional/structural information is known, are to be solubly expressed.

Information relevant to the present invention is disclosed in "Rapid Protein-Folding Assay Using Green Fluorescent Protein" by Geoffrey S. Waldo et al., Nature Biotechnology 17, 691–695 (1999), the teachings of which publication are hereby incorporated by reference herein.

Accordingly, it is an object of the present invention to provide a solubility reporter for rapidly identifying soluble forms of proteins.

Another object of the invention is to provide a method for modifying the solubility of proteins by generating large numbers of genetic mutants of the gene which encodes for the protein to be solubilized which can be expressed and the resulting proteins screened for solubility.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for determining the solubility of a protein, P, of this invention may include the steps of: fusing a DNA fragment, [P], which codes for protein P with the DNA fragment, [R], which codes for a reporter protein, R, forming thereby a fusion DNA fragment, [P-R], which codes for the protein, P-R; ligating the [P-R] fragment into an expression vector to form a plasmid DNA; introducing the plasmid DNA into an expression host such that the fusion protein is overexpressed therein; and detecting protein R in fusion protein P-R, whereby the detection of protein R in fusion protein P-R is an indication that protein P is soluble.

Preferably, the DNA fragment [P] is fused with the DNA fragment [L] which codes for a flexible linker peptide, L, which has been fused with the DNA fragment [R], forming thereby either fusion DNA fragment [P-L-R] or fusion DNA fragment [R-L-P], such that the detection of R in the fusion proteins encoded by [P-L-R] or [R-L-P] is an indication that protein P is soluble.

Preferably also, the DNA fragment bearing [L-R] or [R-L] is part of an expression vector and/or transfection/transformation vector enabling the fusion of [P] to yield the DNA fusions [P-L-R] or [R-L-P] as part of the vectors, thereby enabling a host cell to express either the fusion protein P-L-R or the fusion protein R-L-P, such that the detection of R in the fusion protein P-R is an indication that protein P is soluble.

It is also preferred that the linker peptide is short, flexible, hydrophilic and soluble.

Preferably also, the reporter protein includes green fluorescent protein.

In another aspect of the present invention, in accordance with its objects and purposes, the method for modifying the solubility of a protein, P, hereof may include the steps of: introducing mutations into the DNA fragment [P] which codes for protein P, thereby generating a combinatorial library of mutated variants, [X]; in-frame fusing individual [X] variants with a DNA construct such as a plasmid vector which includes a DNA fragment which codes for a reporter protein, [R], forming thereby a set of DNA constructs containing [X-R] which code for the fusion proteins X-R such that the detection of R in any of the X-R fusion proteins is an indication that the variant protein X contained therein is soluble; introducing each of the DNA constructs into an expression host such that each host cell expresses a unique variant X as a fusion protein X-R therein; and detecting R in X-R, whereby an increase in the detection of R in a host expressing a variant X-R fusion protein relative to that of a host expressing the P-R fusion protein, is an indication that the solubility of variant protein X has increased relative to the solubility of protein P.

Preferably, the DNA fragment [X] is fused with the DNA fragment which codes for a flexible linker peptide, [L], which has been fused with the DNA fragment [R], thereby forming either fusion DNA fragment [X-L-R] or fusion DNA fragment [R-L-X], such that an increase in the detection of R in the fusion proteins expressed by the [X-L-R] or the [R-L-X] is an indication that the solubility of variant protein X has increased relative to the solubility of protein P.

Preferably also, the DNA fragment bearing [L-R] or [R-L] is part of an expression vector and/or transfection/transformation vector enabling the fusion of [X] to yield the DNA fusions [X-L-R] or [R-L-X] as part of said vectors, thus enabling a host cell to express either the fusion protein X-L-R or the fusion protein R-L-X, such that an in crease in the detection of R in the fusion protein is an indication that the solubility of protein X has increased relative to the solubility of protein P.

It is preferred that the linker peptide short, flexible, hydrophilic and soluble.

Preferably also the reporter protein includes green fluorescent protein.

It is also preferred that the step of introducing mutations into [P] generating thereby a combinatorial library of mutated variants [X] is achieved using gene shuffling and directed evolution.

Benefits and advantages of the present invention include the enhancement of the solubility of proteins of interest without having to individually test, (such as by large-scale growth of each mutant in question followed by cell lysis, fractionation and sodium dodecyl sulfate polyacrylamide gel electrophoresis (SDS-PAGE)), the solubility of each protein modification generated, and has general applicability.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Figure 1:
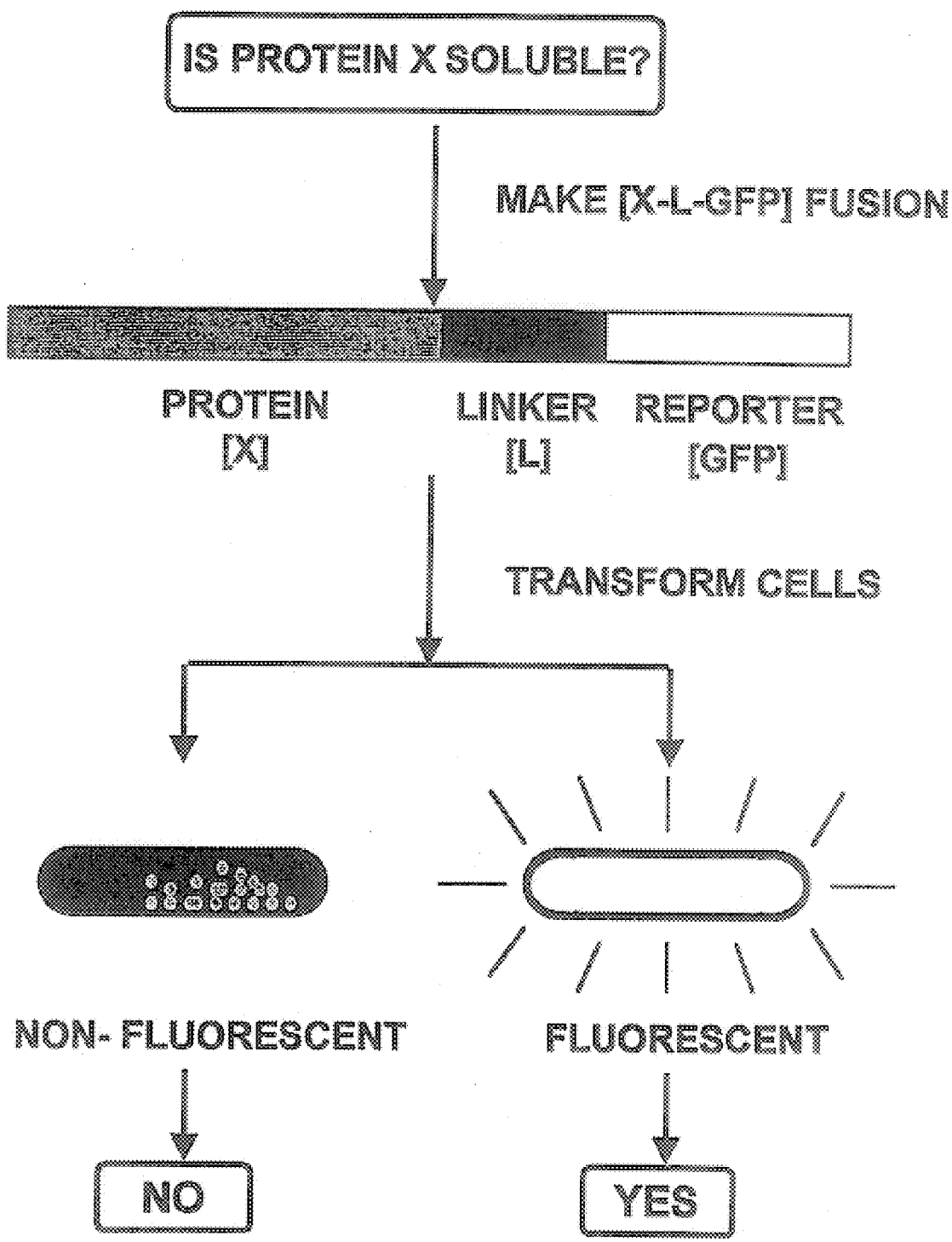
FIG. 1 is a flow diagram illustrating the use of the solubility reporter according to the teachings of the present invention; if protein, P, is insoluble, the detection of the fusion protein, P-L-GFP, is compromised since the fusion protein is poorly fluorescent, while if protein P is soluble, fusion protein P-L-GFP is strongly fluorescent.
Figure 2:
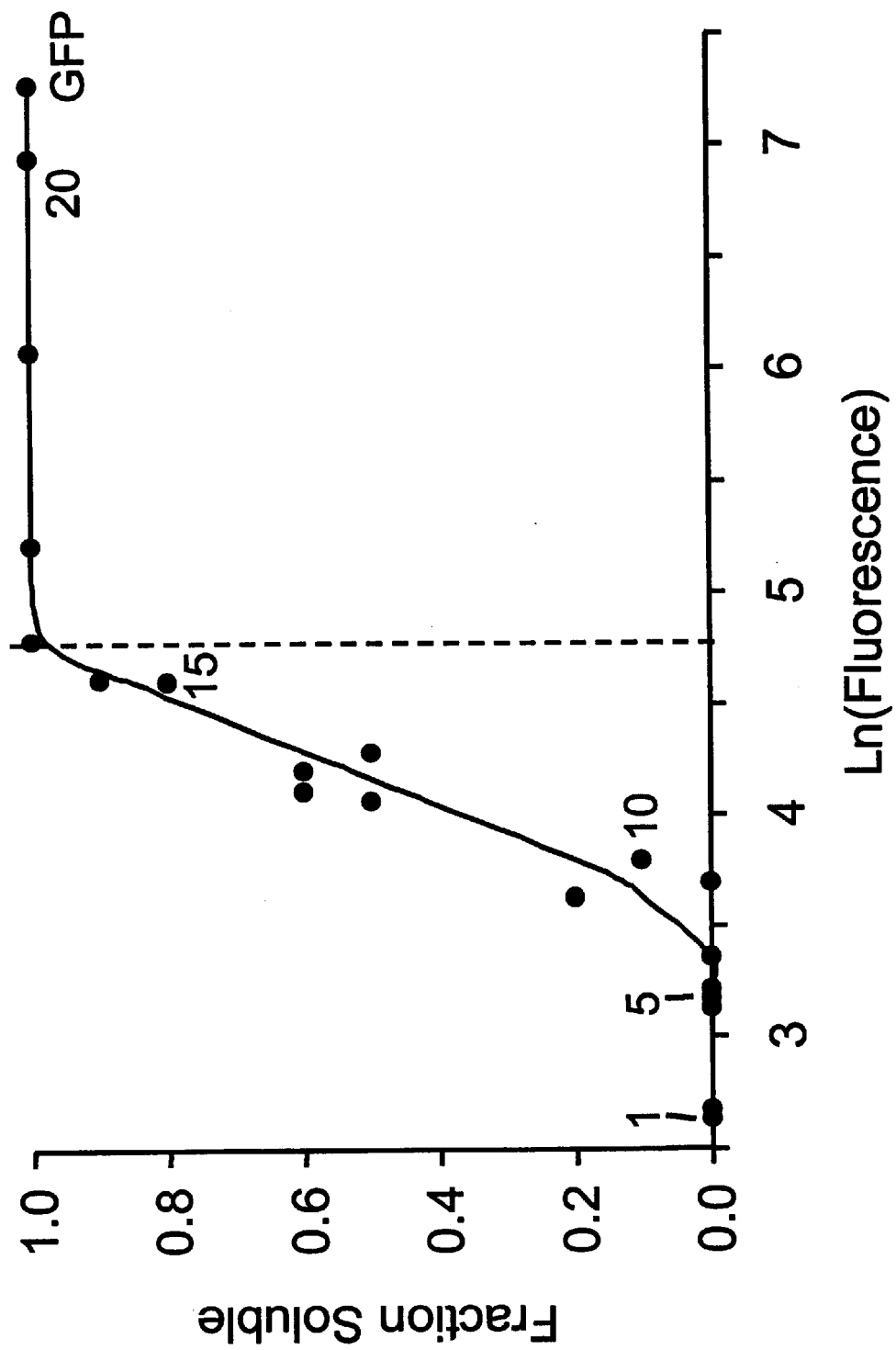
FIG. 2 illustrates the correlation between the solubility of proteins (P) expressed alone and the fluorescence of E. coli cells expressing the proteins as fusions with GFP.

Briefly, the present invention utilizes a solubility reporter protein, expressed by the DNA fragment [R], whose detection level in a fusion protein encoded by the in-frame fusion DNA fragment, [P-L-R] or [R-L-P], provides an assay indicating whether the protein P expressed alone is soluble, where [P] is the DNA fragment which encodes the protein, P, to be solubilized, and [L] is the DNA fragment which encodes a flexible linker peptide, L. In one embodiment of the invention, R is green fluorescent protein (GFP). Linker peptide L, which is preferably optimized for flexibility, hydrophilic nature, and solubility, is fused to the GFP. When overexpressed in the host cell, for example E. coli, the fusion protein(s) L-GFP (GFP fused to the C-terminus of L) or GFP-L (GFP fused to the N-terminus of L) are soluble within the expression host and fluorescent. The DNA encoding P is then fused to a reporter vector containing the DNA fragment which encodes the L-GFP construct, and the fusion protein P-L-GFP (P fused to the N-terminus of L-GFP) is caused to be overexpressed in a host cell. Alternatively, the DNA encoding P is fused to a reporter vector containing a DNA fragment which encodes the GFP-L construct, and the fusion protein GFP-L-P (P fused to the C-terminus of GFP-L) is caused to be overexpressed in the host cell. The GFP-L and L-GFP are chosen such that the observation of GFP fluorescence in the fusion proteins P-L-GFP or GFP-L-P is indicative of P being soluble. It is anticipated that for some systems, linker peptide L will not be required. When P is highly soluble, the GFP fluorescence in the proteins P-L-GFP or GFP-L-P is high within the expression host and such hosts are observed to be highly fluorescent. By contrast, when P is insoluble, the GFP fluorescence associated with the P-L-GFP or GFP-L-P is greatly reduced and the hosts are poorly fluorescent. Thus, P-L-GFP or GFP-L-P constitute solubility reporters for rapidly determining whether P is soluble. FIG. 1 is a schematic representation of the use of the solubility reporter according to the teachings of the present invention. FIG. 2 illustrates the correlation between the solubility of proteins (P) expressed alone and the fluorescence of E coli cells expressing the proteins as fusions with GFP, where proteins from Pyrobacullum aerophilum are selected in order of increasing GFP fusion fluorescence as follows: (1) tartrate dehydratase beta subunit; (2) nucleoside-diphosphate kinase; (3) tyrosine tRNA synthetase; (4) polysulfide reductase subunit; (5) methyltransferase; (6) GTP cyclohydrolase I; (7) aspartate-semialdehyde dehydrogenase; (8) purine-nucleoside phosphorylase; (9) soluble hydrogenase; (10) cysteine tRNA synthetase; (11) 3-hexulose 6-phosphate synthase; (12) nirD protein; (13) C-type cytochrome biogenesis factor; (14) phosphate cyclase; (15) hydrogenase expression/formation protein (hypE); (16) chorismate mutase; (17) DNA-directed RNA polymerase; (18) ribosomal protein S9p; (19) translation initiation factor; (20) sulfite reductase (dissimilatory subunit); and GFP is a soluble variant of GFP expressed alone. The dashed line indicates the threshold above which the test proteins are fully soluble.

Figure 3:
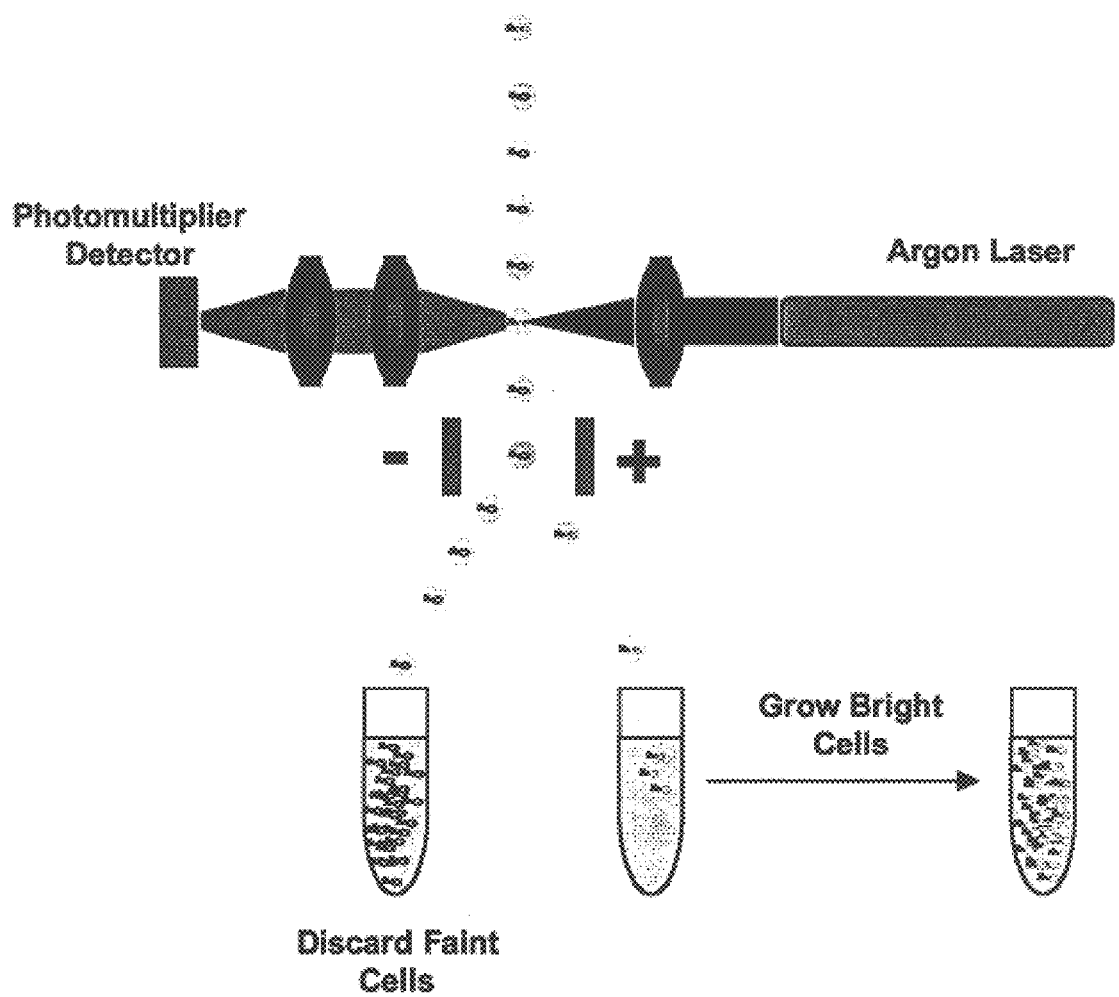
FIG. 3 is a schematic representation illustrating the use of fluorescence-assisted cell sorting to identify and select mutated versions of a chosen protein which have enhanced solubility by virtue of the improved fluorescence of cells expressing the mutants as GFP fusion proteins.

Modification and, more particularly, enhancement of the solubility of protein P is accomplished by use of a DNA construct which includes the solubility reporter DNA fragments [L-GFP] or [GFP-L], in a directed evolution of [P]. A combinatorial library of mutated variants X is first generated by gene shuffling, as an example. The resulting pool of genes [X] encoding mutated proteins X is then genetically fused in-frame either with a pool of DNA constructs such as vectors containing [L-GFP] to produce a pool of DNA constructs encoding fusion proteins X-L-GFP, or with a pool of DNA constructs containing [GFP-L] to produce a pool of DNA constructs encoding fusion proteins GFP-L-X. After introducing the DNA into an expression host, such as electroporation of circular plasmid vectors into E. coli, individual variants with increased fluorescence (and therefore increased solubility) may be screened and separated using fluorescence-assisted cell sorting, as an example, since the observation of GFP fluorescence a fusion variant is an indication of the solubility of X. Millions of variants can be screened in 20 minutes. Further cycles of directed evolution may be instigated until no further improvement in solubility is observed. Furthermore, mutations which are unnecessary for enhanced solubility which accumulated during the directed evolution, can be removed by in vitro recombination or backcrossing of the DNA encoding enhanced variants X of P against an excess of DNA encoding wild type P, followed by selection of variants retaining enhanced solubility, using the solubility reporter procedure of the present invention. FIG. 3 is a schematic illustration of the generation of mutated versions of a selected protein, P, where fluorescence-assisted cell sorting (FACS) is used to identify and select mutants with enhanced solubility in according to the teaching of the present invention.

The present invention, then, requires establishing the relationship between the detection of R in the fusion proteins (P-R, R-P, P-L-R, R-L-P), and the solubility of P by itself (in a non-fusion situation). To establish this calibration, the steps required may include: determining the solubilities of a group of selected proteins by SDS-PAGE, for example; detecting R in fusion proteins with the same set of proteins; plotting the solubility of each protein P as a function of the level of detection of R when fused with P; and fitting a smooth line to the resulting data points. The resulting relationship permits the prediction of the solubility of unknown proteins given the level of detection of R in associated fusion proteins.

The appropriate method of detection for R is dependent on the manner in which R functions. If R is chosen to be green fluorescent protein, then fluorescence detection of the fusion protein incorporating R in vivo or in vitro, using a fluorimeter, for example is utilized. If R is an antibiotic resistance protein with enzymatic function, then in vivo detection may include the determination of the antibiotic resistance of cells containing the fusion protein to the antibiotic, while in vitro detection of the enzymatic activity of the antibiotic resistance protein could consist of colorimetric assays for the function of the antibiotic resistance protein, for example. It is preferable but not essential that R is a positive indicator of the solubility of protein P, such that as the solubility of said test proteins increases, the detection of the function of R in the fusion protein context also increases.

To screen large numbers of versions of an arbitrary protein, it is desirable, but not essential, that linker protein L and reporter protein R be chosen to have the following characteristics: (1) The observed parameter for R, in the fusions X-L-R and R-L-X, must not be observable independent of the solubility of X or by the presence of X; (2) the solubility of R should not determine the detection of R in X-L-R or R-L-X; (3) The detection of R in X-L-R and R-L-X should be positively correlated with the solubility of X expressed alone; (4) R should not assist the folding of X; (5) L should not significantly influence the detection of R in any of R-L-X or X-L-R; and (6) L should not dominate the folding of any of X, R, X-L-R, or R-L-X.

Having generally described the invention, the following EXAMPLES illustrate the application of the method of the present invention in greater detail.

EXAMPLE 1

As an example of the assembly of a construct which satisfies the above-described six criteria, a Bgl-II/Xho-1 fragment of plasmid pET-21a(+), containing: the T7 promoter; lac operator sequence; ribosomal binding site; and multiple cloning site was ligated into the Bgl-II/Xho-1 site of pET-28a(+). The resulting hybrid plasmid contained the Kan, lac, and F1 origin of replication of the pET-28a(+) backbone. The pET21a(+) and pET28a(+) vectors were used as obtained from a commercial source. The vector was digested with Nde-1 and BamH-1, the small fragment was discarded, and replaced with an in-frame stuffer such that the sequence, inclusive of the Nde-1 and BamH-I sites, was [CATATGTGTAGACAGCTGGGATCC] (SEQ ID No. 1). Next, the vector was digested with BamH-I and EcoR-1 and the small stuffer was discarded. The BamH-I/EcoR-1 site was filled with the DNA fragment [GGATCCGCTGGCTCCGCTGCTGGTTCTGGCGAAT-TC] (SEQ ID No. 2), coding for the flexible linker L (GSAGSAAGSGEF) (SEQ ID No. 3). An improved variant of GFP was created by site-directed mutation using recombinant PCR (see, e.g., "Recombinant PCR" by Russel Higuchi in "PCR Protocols, a Guide to Methods and Applications", Michael A. Innis, David H. Gelfand, John J. Sninsky, and Thomas J. White, eds. Academic press, Inc., 177, (1990)), of the soluble variant of Crameri et al., supra, to yield the red-shift S65T mutation (See, e.g., "Improved Green Fluorescence," by Roger Heim et al., Nature 373, 663, (1995)) which improves the performance of the protein in FACS, by increasing the absorption of the fluorophore of 488 nm light (near the argon laser emission commonly used for FACS). The internal Nde-1 and BamH-1 sites were abolished by silent-mutation. The resulting GFP variant was amplified by PCR using the 5' primer [GATATAGAATTCAGCAAAGGAGAAGAACTTTTC] (SEQ ID No. 4), incorporating a 5' EcoR-1 site; and the 3' primer [GAATTCGGTACCTTATTTGTAGAGCTCTA-CCAT] (SEQ ID No. 5), incorporating a 5' Xho-1 site. The resulting vector was digested with EcoR-1/Xho-1, the stuffer discarded, and replaced with the EcoR-1/Xho-1-digested EcoR-1:GFP:Xho-1 amplicon, and the circular plasmid produced thereby was transformed by electroporation into the $E.\ coli$ strain BL21(DE3) genotype: (F$^-$ ompT hsdS$_B$ (r$_B^-$ m$_B^-$) gal dcm (DE3)), a commercially available strain. The construct in the pET vector system is inducible by IPTG. A transformant was used to inoculate a culture of LB and grown to an optical density (O.D.) at 600 nm of approximately 0.5, IPTG was added to a final concentration of 1 mM, and induction was allowed to proceed for 2 h. The bright green fluorescence, visible under room lighting, indicated that the fusion construct was soluble and well-expressed. Next, the small in-frame stuffer fragment between Nde-1 and BamH-1 was removed by restriction digest, and replaced by an out-of-frame stuffer with 3 translational stops. Cells expressing this fusion were non-fluorescent due to termination of translation prior to the GFP. Finally, the vector was digested with Nde-1+BamH-1 to remove the stuffer and create a recipient site for Nde-1/BamH-1 flanked inserts. This recipient vector is subsequently referred to as the solubility-reporter vector. The specific examples described below use primers for the genes of interest which contain Nde-1(N-terminus) and BamH-1 (C-terminus). The use of an out-of-frame stuffer insures that and vectors escaping digest code for non-fluorescent constructs and thus had the effect of eliminating false-positives. To test the protein solubility reporter, 20 different proteins were expressed from the hyperthermophilic archeon $Pyrobaculum\ aerophilum$ (see, e.g., Fitz-Gibbon, S. et al. "A fosmid-based genomic map and identification of 474 genes of the hyperthermophilic archaeon $Pyrobaculum\ aerophilum$." Extremophiles 1, 36–51 (1997)), in $E.\ coli$ at 37° C. as N-terminal GFP fusions. Gene-dependent differences (up to 50-fold) in whole cell GFP fluorescence were directly related to the fraction of the overexpressed protein found in the supernatant of lysed cells expressing the corresponding non-fusion protein under identical conditions (see FIG. 2 hereof). The correlation between non-fusion solubility and GFP fusion fluorescence is not perfect. For example, the solubility of protein 8 (purine-nucleoside phosphorylase) is underestimated, while that of protein 9 (soluble hydrogenase) is overestimated (see FIG. 2 hereof). Nonetheless, failure of the GFP chromophore to be detected in the fusion context is well correlated with the likelihood that the protein of interest will be aggregated when expressed without the GFP tag.

The detailed experimental protocol for cloning the various test proteins is as follows. Genes coding test proteins were amplified by conventional PCR from plasmids available in-house (gene-5 and xylR), plasmids purchased from commercial sources (maltose binding protein, malE, Invitrogen), or genomic DNA (Pyrobaculum aerophilum). Bullfrog H-subunit and L-subunit ferritin genes were cloned from Rana catesbeiana tadpole red cells by RT-PCR using a commercially available kit. Gene-5 C33(TGT)→T33(ACT) was engineered using conventional PCR techniques. Incorporating two codon changes guarded against trivial mutation to the soluble wild type sequence; that is, by the reversion T33C in subsequent directed evolution experiments. Clones were isolated and sequences verified by dye-terminator sequencing. Specific ferritin mutants were engineered by overlap PCR.

EXAMPLE 2

GFP-fusion solubility reporter assay was also demonstrated to be possible for cell-free extracts using six proteins of bacterial and vertebrate origin. In an in vitro protein synthesis system, the bulk concentration of newly synthesized polypeptides is reduced by a factor of at least 1000 relative to their concentration in *E. coli* (see, e.g., Zubay, G. "In vitro synthesis of protein in microbial systems." Ann. Rev. Genet. 7, 267–287 (1973), and Neidhardt, F. C. Chemical composition of *Escherichia coli*. Neidhardt, F. C., ed. in *Escherichia coli* and *Salmonella typhimurium*: Cellular and Molecular Biology, pp. 3–6, American Society of Microbiology, Washington, D.C. (1987)). The production of the fluorescent GFP fusion protein was initiated by addition of the DNA template, and appeared to be complete within ca. 30 min at 37° C. When normalized by a control expressing GFP alone, the GFP fusion fluorescence in the in vitro system and in *E. coli* closely agreed as shown in Table 1.

TABLE 1

GFP fusion fluorescence from in vivo and in vitro expression

| Type of Protein | *E. coli* cells[a] | Coupled transcription + translation[b] |
|---|---|---|
| Insoluble proteins | | |
| Bullfrog H-subunit ferritin | 0.034 ± 0.004 | 0.031 ± 0.003 |
| Gene-V (C33T) | 0.030 ± 0.005 | 0.041 ± 0.005 |
| XyIR | 0.023 ± 0.003 | 0.031 ± 0.003 |
| Soluble proteins | | |
| Bullfrog L-subunit ferritin | 0.58 ± 0.02 | 0.53 ± 0.03 |
| Gene-V (wt) | 0.40 ± 0.03 | 0.43 ± 0.02 |
| Maltose binding protein | 0.43 ± 0.02 | 0.50 ± 0.03 |

[a]*E. coli* cells: whole cell fluorescence measured by fluorimetry expressing indicated proteins as fusions with GFP at 37° C., normalized by intensity of *E. coli* expressing GFP alone.
[b]Coupled transcription+translation: Fluorescence of coupled *E. coli* S-30 transcription/translation reactions using circular plasmid templates, normalized by fluorescence of reaction using GFP template. Experiments were performed in triplicate. Note that the ratioed fluorescence data is dimensionless.

The detailed experimental protocol for the in vitro coupled transcription/translation reactions is as follows. Plasmids were isolated from 3-ml overnight cultures using a commercially available spin-column purification kit. DNA concentrations were determined spectrophotometrically at 260 nm, plasmids were diluted to 0.1 µg/µl, and 10 µl added to a 150 µl coupled transcription/translation mix (*E. coli* T7 S30 extract system for circular DNA, Promega (Madison, Wis.) according to manufacturer instructions. Although the development of green fluorescence appeared complete within 30 min, the reaction was allowed to proceed for 2 hr at 37° C. Fluorescence was measured by spectrofluorimetry (excitation 490 nm, emission 510 nm, each with 5 nm band width). A small background resulting from the endogenous fluorescence of the translation mix was subtracted during data analysis, and the fluorescence of each test samples was normalized by dividing by the fluorescence of a sample translating GFP alone.

The detailed experimental protocols for determining fluorescence and protein solubility are next described. Cultures were grown at 37° C. in Luria-Bertani (LB) media containing 30 µl/ml kanamycin and induced with 1 mM isopropylthiogalactoside (IPTG) at indicated temperature. Cells were diluted to $OD_{600}$ nm=0.15 in 10 mM TRIS, pH=7.5, 0.15 M NaCl, (buffer A), and fluorescence was measured using a spectrofluorimeter (excitation 490 nm, emission 510 nm, each with 5 nm band width). Protein solubility was determined by SDS-PAGE throughout (see, e.g., Zhang, Y. et al. Expression of eukaryotic proteins in soluble form in *Escherichia coli*. Protein Expr. Purif. 12, 159–165 (1998)). A 3 ml culture of cells was pelleted in a 1.5 ml eppendorf tube and washed twice with 1 ml of buffer A. The pellet was resuspended in 150 µl of buffer A and subjected to two sequences of 10 pulses of sonication, using a sonicator equipped with a ½" horn and ⅛" tapered tip, with a minimum power setting and 80% duty cycle. The sample was pelleted by centrifugation between the two pulse sequences. The sonicant was centrifuged at 14,000 g for 15 minutes and the supernatant fraction removed by pipetting and reserved. The remaining pellet was washed twice with 1 ml buffer A, and finally resuspended in 150 µl buffer A. 5 µl of the sample (pellet or supernatant) was mixed with 5 µl of sodium dodecylsulfonate buffer containing dithiothreitol and heated for 15 min at 100° C. in a MJR PTC-200 thermocycler (heated lid). The denatured proteins were resolved by sodium dodecylsulfonate-polyacrylamide electrophoresis (SDS-PAGE) using a 12.5% acrylamide homogeneous gel, stained by Coomassie brilliant blue dye, and fixed. The gels were scanned using a flatbed scanner, and densitometry analyzed using NIH Image. The total expressed protein was estimated by summing the integrated density of the soluble and insoluble fractions $D_T=D_S+D_I$. The soluble fraction was defined as $S_F=D_S/D_T$, while the insoluble fraction was defined as $I_F=D_I/D_T$. The SDS sample buffer included 2 mg/ml of bovine serum albumin (BSA) to provide an internal density standard compensating for differences in loading volume. Prior to processing, all integrated sample densities were thus normalized by the BSA integrated sample density.

EXAMPLE 3

Figure 4A:
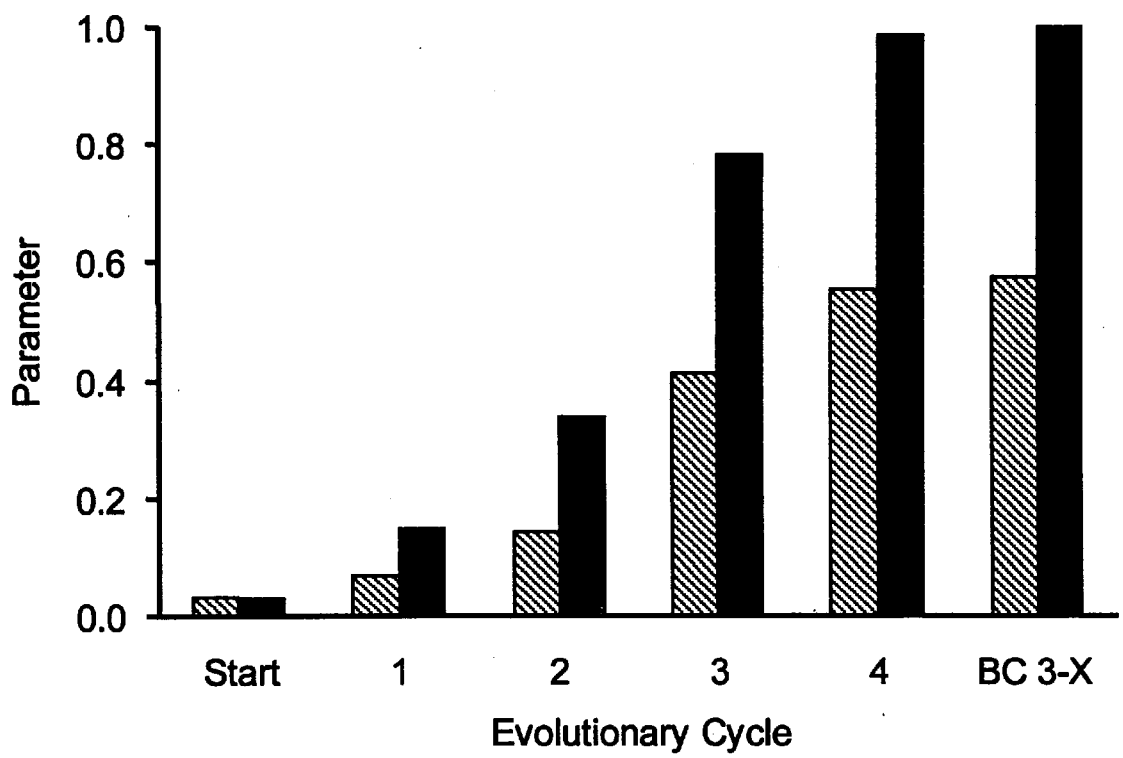
FIGS. 4a and 4b show the improved solubility of non-fusion (black bars) proteins and GFP fusion protein fluorescence (crosshatched bars) for: gene-V(C33T) and bull frog H-subunit ferritin, respectively, after each of four successive directed evolution cycles.
Figure 4B:
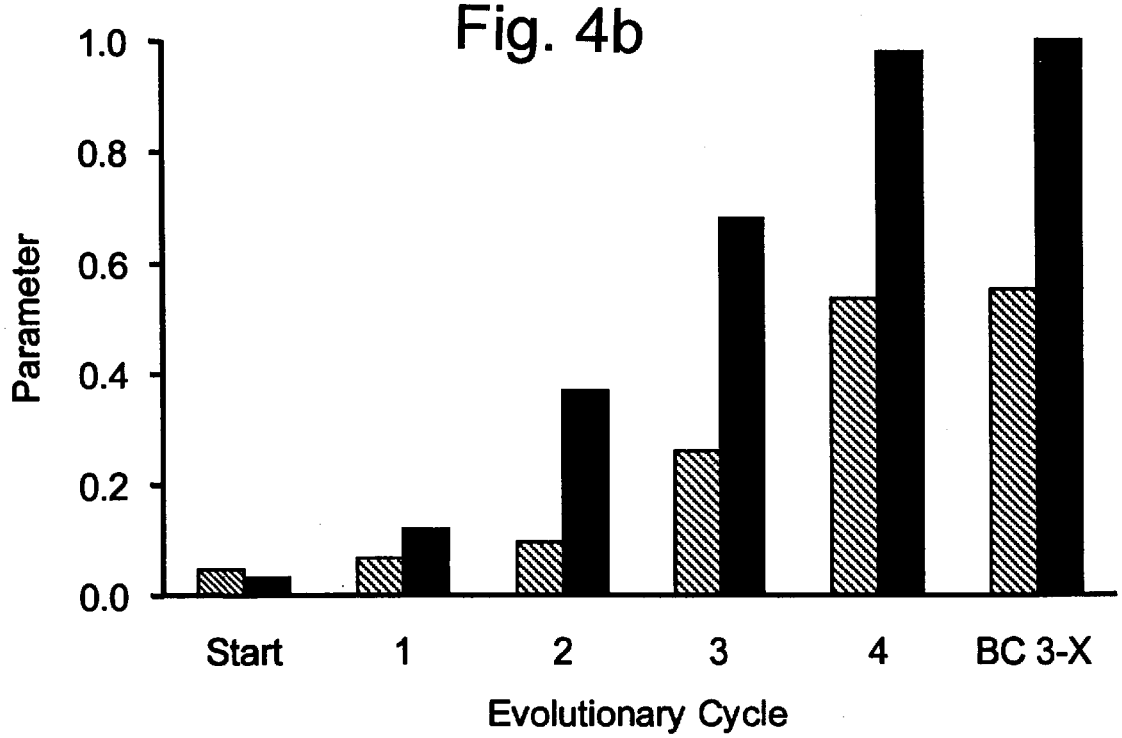

Empirically, the GFP solubility reporter distinguishes proteins that fold robustly and are highly soluble when expressed in *E. coli* from those that tend to aggregate. Such a reporter system could be used in a directed evolution process, (see, e.g., Arnold, F. H. "Directed evolution: Creating biocatalysts for the future." Chem. Eng. Sci. 51, 5091–5102 (1996), and Zhao, H. M. and Arnold, F. H. "Optimization of DNA shuffling for high-fidelity recombination." Nuc. Acids Res. 25, 1307–1308 (1997)), to evolve proteins that are normally insoluble into closely related ones with improved solubility. As a test of directed evolution of protein solubility, the mutant C33T of gene-protein was chosen (see, e.g., Terwilliger, T. C., Zabin, H. B., Horvath, M. P., Sandberg, W. S. and Schlunk, P. M. "In-vivo characterization of mutants of the bacteriophage-F1 gene-V protein isolated by saturation mutagenesis." J. Mol. Biol. 236, 556–571 (1994)), and bullfrog H-subunit ferritin (see, e.g., Dickey, L. F. et al. "Differences in the regulation of messenger-RNA for housekeeping and specialized-cell ferritin: a comparison of 3 distinct ferritin complementary DNAs, the corresponding subunits, and identification of the 1st processed pseudogene in Amphibia." J. Biol. Chem. 262, 7901–7907 (1987), and Waldo, G. S. and Theil, E. C. "Ferritin and Iron Biomineralization", Comprehensive Supramolecular Chemistry 5, pp. 65–91, Susslick, K. vol. ed., Pergamon Press, U.K., (1996)). Beginning with DNA encoding the insoluble wild-type proteins, we used DNA shuffling (see, e.g., Stemmer, W. P. C. "Rapid evolution of a protein in-vitro by DNA shuffling." Nature 370, 389–391 (1994)) to generate and recombine mutations, and the GFP solubility reporter to identify variants with improved folding. Each protein was subjected to four rounds of forward evolution to generate soluble variants, followed by three rounds of backcrossing (Stemmer, supra) against parental DNA to remove non-essential mutations. Bullfrog H-subunit ferritin or gene-V (C33T) PCR amplicons were DNAse-I digested and in vitro recombined (see, e.g., Arnold, supra (1996)) with the following modifications: Co(II) was used in place of Mn(II) as the DNAse-I metal cofactor, Pfu(exo+) DNA polymerase was used during forward mutation, and Pfu(exo+) DNA polymerase was used for backcrossing for high-fidelity amplification. Reassembled genes were cloned into the GFP fusion vector, and transformed into *E. coli* strain DH10B by electroporation, yielding ca. $5 \times 10^6$ unique clones. Plasmids isolated from the plates were transformed into BL21 (DE3) (Novagen, Madison, Wis.). Cells were plated directly onto nitrocellulose membranes at a density of ca. 2000 transformants/plate, grown at 37° C. for 9–12 hr until ca. 1 mm dia., then the membranes were transferred to LB/Kan plates containing 1 mM IPTG, and induced for 3 hr at 37° C. The 40 brightest clones were picked, maintained as individual permanents, and as pools. DNA from these optima was used in subsequent rounds of directed evolution. A total of 10,000 clones were screened for each cycle of forward evolution. For backcrossing, amplicons derived by PCR from a plasmid isolation of the pooled optima were combined in a 1:2 ratio with PCR amplicons of wild type DNA. DNAse-I digest and subsequent protocols as described above for the forward evolution. With each cycle of evolution, both the non-fusion solubility and GFP-fusion fluorescence increased as shown in FIG. 4 hereof. Forty clones expressing GFP fusions were pooled and the normalized fluorescence determined at 37° C., as described hereinabove. Vector DNA prepared from these pools was digested and the insert subcloned en masse into an expression vector without the GFP tag. Solubility of pooled non-fusion proteins was expressed at 37° C. Evolved gene V(C33T) and H-subunit ferritin pools were assayed after backcrossing three times.

Figure 5A:
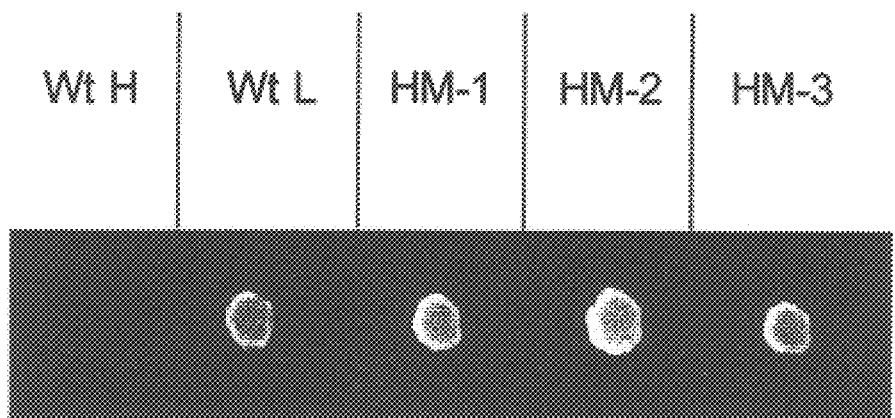
FIGS. 5a–c are a photograph of E. coli colonies expressing GFP fusions of ferritin variants (FIG. 5a), a Coomassie-stained 12.5% acrylamide SDS-PAGE of soluble (S) and pellet (P) fractions of ferritin variants expressed without GFP tags (the upper band is bovine serum albumin (BSA) and the position of H and L wild-type ferritins are shown) (FIG. 5b), and an Fe activity blot assay of nonfusion proteins (FIG. 5c), where the column marked wt H, indicates insoluble wild type H-subunit ferritin; the column marked wt L indicates soluble wild type L-subunit ferritin; and the columns marked HM-1, HM-2, and HM-3, indicate soluble, evolved ferritin optima after backcrossing to remove non-essential mutations.
Figure 5B:
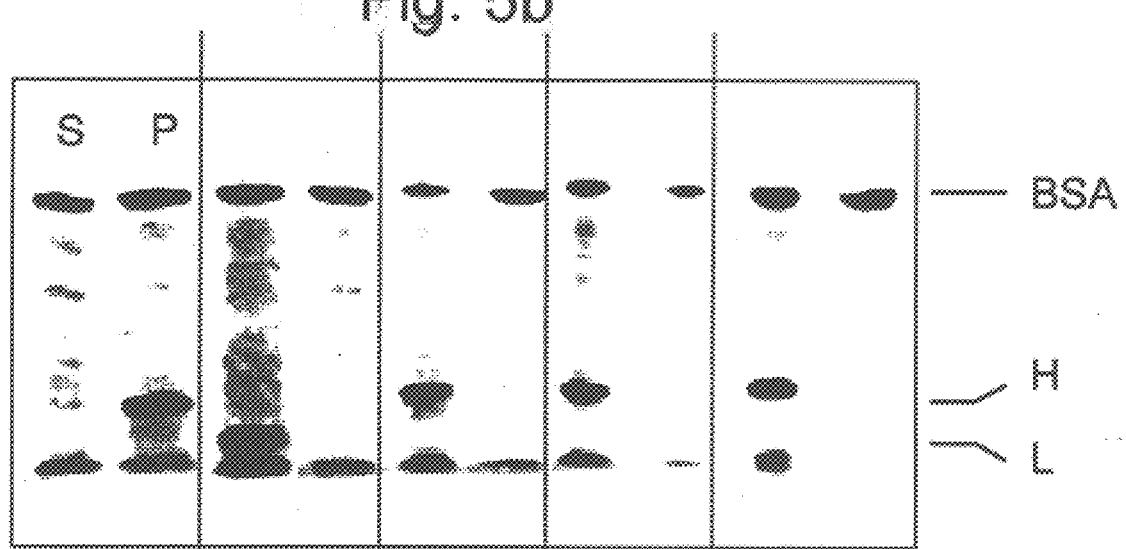

The rapid Fe-mineralization phenotype of H-subunit ferritin requires at least 7 key amino acids (see, e.g., Harrison, P. M. and Arosio P. "The ferritins: molecular-properties, iron storage function and cellular-regulation." Biochim. et Biophys. Acta-Bioenerg. 1275, 161–203 (1996)). Thus the ferritin system can be used to test whether directed evolution of protein folding can be accomplished without a loss of function. Thirty of the ferritin clones that were most fluorescent when expressed as GFP fusions were sequenced by dye-terminator sequencing. These comprised three variants which were designated: HM-1 (N47D+Q55L+E58R+T93P+G146E), HM-2 (N47D+E58K+E59A+T93P+G146E) and HM-3 (K53R+Q55R+T93P+G146E). HM-3 also contained two 'silent mutations' D120 (GAG to GAC) and Q138 (CAG to CAA). These changed the codon usage without changing the amino acid coded for. The variants HM-1 and HM-2 each contain a substitution of E58, an acidic amino acid residue involved in iron binding and ferroxidation (see, e.g., Harrison, supra), by a basic amino acid unlikely to bind iron. Aside from this substitution none of the 7 residues directly involved in the function of ferritin were mutated. All three evolved ferritin variants were highly fluorescent as GFP fusions as shown in FIG. 5a hereof and fully soluble when expressed as non-fusions in *E. coli* at 37° C. as shown in FIG. 5b hereof. These proteins were assayed for enzymatic activity by measuring their ability to oxidize Fe(II). Supernatant fractions of 3-ml cultures were diluted to ca. 1 mg/ml in ferritin. The concentration of ferritin was determined by SDS-PAGE gel densitometry scan using NIH-Image, (NIH-Image is a public domain image processing program developed at the U.S. National Institutes of Health and available on the Internet, relative to a ferritin sample of known concentration. For ferroxidase assays, 3 μl aliquots of protein were dofted onto a moist nitrocellulose membrane on a stack of two Whatman 3M filter paper disks soaked in 50 mM MES, pH=6.0, 0.15 M NaCl (Buffer B). The membrane with the bound ferritin was transferred to a stack of two filters soaked in Buffer B containing 0.1 mM Fe(II), for 5 min at 30° C. The reaction was quenched by washing the membrane twice in Buffer B containing 5 mM EDTA to remove adventitiously bound Fe(II). The Fe(II) zones were developed (see, e.g., Moos, T. and Moligard, K. "A sensitive post-DAB enhancement technique for demonstration of iron in the central-nervous-system." Histochem. 99, 471–475 (1993)). Briefly, the membrane was treated with a solution of 1% HCl+1% potassium ferrocyanide (Turnbull Blue reaction) at ambient temperature (ca. 24° C.) for 10 min. After copious washing with distilled water, the Prussian Blue spots were intensified by treating with 10 mM $H_2O_2$+10 mM DAB (diamminobenzidine) in 10 mM TRIS pH=8.0 (Buffer C), for 5 min in the dark. The membrane was copiously washed with distilled water, transferred to a petri plate, and scanned on a flatbed scanner while still moist.

Figure 5C:
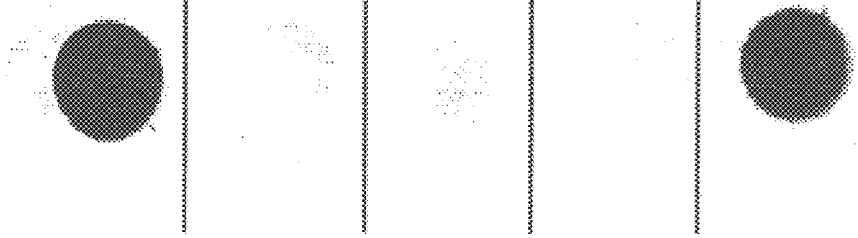

HM-1 and HM-2 were non-functional. The third variant, HM-3, retained most of the wild type Fe-oxidation activity as illustrated in FIG. 5c hereof, showing that directed evolution of solubility using GFP as a solubility reporter can generate mutants of a protein of interest with improved solubility while maintaining function of the protein of interest.

EXAMPLE 4

The above-described use of a solubility reporter can be analogously extended to determine the solubility of protein fragments. For example, to determine the solubility of fragments F of a protein P, the DNA [P] is subjected to a partial enzymatic digest, (e.g., by DNASE-I in the presence of the divalent cations $Mn^{2+}$ or $Co^{2+}$), to create a pool of smaller fragments, [F]. The fragments can be polished with a proof-reading polymerase bearing 3'–5' exonuclease activity to yield blunt-ends, or subsequently given A-overhangs by treatment with a polymerase devoid of 3'–5' exonuclease activity with excess dATP (e.g., Taq polymerase). If desired, a particular size range of the fragments [F] may be selected, by agarose gel electrophoresis as an example. After ligation (e.g., blunt-end or T/A overhang) with the pool of appropriate recipient solubility reporter vector (e.g., bearing a blunt-end or T/A cloning site in-frame with [L-R]), some of the fragments [F] will form in-frame translational fusions, [F-L-R]. After transformation into an appropriate host, (e.g., *E. coli*), expressed fusion proteins F-L-R which contain a soluble fragment F will be detectable in the host by virtue of R (e.g., if R is GFP the host cells will be fluorescent). Thus, the above-described solubility reporter method may be used to determine the solubility of a protein, its variants (mutants), and fragments thereof.

EXAMPLE 5

EXAMPLE 1 has shown that GFP can be used as a solubility reporter. However, solubility reporters incorporating a translational fusion [P-L-R] include systems in which R is a protein/peptide other than GFP. When the fusion construct [P-L-R] is used, R can be a protein/peptide which gives a detectable signal observable by suitable chemical, biological or physical means, when linked to P-L as P-L-R. As an example, R could be the beta-galactosidase enzyme, lacZ. Clones expressing P-L-lacZ in which P is a soluble protein are detected by the enzymatic activity of lacZ (See, e.g., "Beta-Galactosidase Gene Fusions For Analyzing Gene Expression In *Escherichia Coli* And Yeast," by M. Casadaban et al., Methods Enzymol. 100, 293 (1983)) on substrates which yield a colored reaction product (For example, X-gal (5-bromo-4-chloro-3-indolyl-β-D-galactoside)). Colonies expressing fusion proteins with β-galactosidase activity turn blue on plates containing X-gal. Furthermore, in situations where the lacZ protein proves too large, the functionally complementable lacZα fragment is used as a substitute. The complementary fragment Δ-lacZ is provided by the host chromosome (For example, *E. coli* strain DH10B (F$^-$ mcrA Δ(mrr$^-$hsdRMS-mcrBC) φ80dlacZΔM15 ΔlacX74 deoR recA1 endA1 araD139 Δ(ara,leu)7697 galU galKλ$^-$ rpsL nupG), where the complementary fragment is provided by φ80dlacZΔM15. Fusion proteins P-L-lacZα containing a soluble protein P are soluble and contain a correctly-folded lacZα, thereby leading to complementation of the Δ-lacZ fragment and restoration of lacZ β-galactosidase activity.

EXAMPLE 6

Reporter proteins R, which have optimal activity when present in a non-fusion context may be employed for assays. The construct P-L-C-R is generated, where C is a unique protease site. For example, C could be the viral protease cleavage site for the plum pox virus NIa protease (See, e.g., M. Martin et al., "Determination of polyprotein processing sites by amino terminal sequencing of nonstructural proteins encoded by plum pox polyvirus", Virus Res. 15, 97, (1990)), and R is the lacZα fragment, as an example. The construct P-L-C-lacZα and the viral protease (NIa) could each be expressed under the control of separately inducible promoters on separate plasmids with compatible origins of replication. For an example of the use of multiple compatible plasmids with cloning sites under independently controlled promoters, see R. Lutz and H. Berjard, "Independent and tight regulation of transcriptional units in *E. coli* via the LacR/O, the TetR/O and AraD/I$_1$-I$_2$ regulatory elements", Nucleic Acids Res., 25(6), 1203, (1997). The plasmids and required *E. coli* host strains are commercially available; for example, the P-L-C-lacZα construct could be expressed under the control of the tet promoter, and the NIa gene under the control of the arabinose promoter/repressor. The plasmid (s) would be transformed into the appropriate *E. coli* host (see Lutz, supra), and anhydrotetracycline added to the growth medium to induce expression of P-L-C-lacZα. After accumulation of the fusion protein P-L-C-lacZα, arabinose+ IPTG is added to the growth medium to induce expression of the NIa protease. P-L-C-lacZα is soluble and contains a correctly-folded lacZα domain, and P-L-C-lacZα is cleaved at site C, only if P were soluble. Subsequent release of lacZα complements the Δ-lacZ fragment and restores lacZ β-galactosidase activity, which is detected by standard colorimetric or fluorometric assays for β-galactosidase activity.

EXAMPLE 7

As another example, R might be an antibiotic selection marker such as the β-lactamase gene (bla), which confers resistance to penicillin-derived antibiotics commonly used in cloning vectors. Antibiotic resistance proteins active in the cytoplasm of *E. coli* or other hosts (such as the commonly used proteins conferring resistance to chloramphenicol, kanamycin, and zeocin) would be capable of conferring resistance to the specific selection agent while still fused to the protein of interest. However, the β-lactamase gene contains a signal peptide and is translocated to the periplasm of *E. coli*. However, proper processing of the antibiotic resistance protein and translocation to the periplasm would be impeded by N-terminus fusions, although cleavage by the protease obviates this problem. The P-L-C-β-lactamase fusion protein would be soluble only if P were soluble. Concomitant induction by both anhydrotetracycline and IPTG+arabinose would provide both the fusion protein P-L-C-β-lactamase and the viral cleavage protease NIa. In cells bearing soluble variants of P, the fusion protein P-L-C-β-lactamase would be soluble and cleaved at C by virtue of the protease NIa, releasing functional β-lactamase resistance protein, thereby conferring antibiotic resistance to the antibiotic ampicillin. Conversely, in cells bearing non-soluble variants P, the fusion protein would be insoluble, the protease cleavage site C would be buried in inclusion bodies, and thereby inaccessible to cleavage by the viral protease. Furthermore, the β-lactamase protein would be buried in inclusion bodies, misfolded and non-functional. Such cells would not have resistance to the antibiotic ampicillin. It would be apparent to those having skill in the biochemical arts that selection for cells bearing soluble variants of P (and therefore having antibiotic resistance) could be accomplished by challenging mixtures of the above-mentioned cells by supplying the selective agent (e.g., the antibiotic ampicillin) in the growth medium. Moreover, it is likewise apparent to one having skill in the art that both the fusion protein P-L-C-β-lactamase and the protease NIa must be made continuously available to confer antibiotic selection throughout the life of the cell, and thus both genes must be simultaneously induced (in this example, by providing both anhydrotetracycline and IPTG/arabinose in the growth media). Cells with antibiotic resistance will survive, thereby selecting for soluble variants of P. Furthermore, additional improvement in the solubility of such variants could be accomplished by increasing the concentration of selective agent (e.g. ampicillin) during subsequent rounds of recombination and selection.

The foregoing description of the invention has been presented for purposes of illustration and description and is not intended to be exhaustive or to limit the invention to the precise form disclosed, and obviously many modifications and variations are possible in light of the above teaching. For example, it would be apparent one having skill in biochemistry after reviewing the present disclosure that the method of the present invention can be implemented in insect, yeast and mammalian cells, wherein fusion proteins P-L-GFP are expressed to create a solubility reporter. Similarly, directed evolution for improving the solubility of proteins can be performed using insect cells, and the required DNA manipulation according to the teachings of the present invention can be achieved in vitro or in vivo.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determining whether a protein P is soluble, said method comprising the steps of:
   a. fusing a DNA fragment [P], which codes for protein P, with a DNA fragment [R], which codes for a reporter protein R, forming thereby a fusion DNA fragment [P-R], which codes for the fusion protein P-R, such that the detection of R in P-R correlates with solubility of protein P;
   b. expressing the fusion DNA fragment [P-R] such that fusion protein P-R is produced; and
   c. detecting the reporter protein R in the fusion protein P-R, wherein the reporter protein R is green fluorescence protein (GFP).

2. A method for determining the solubility of a protein, said method comprising the steps of:
   a. fusing a DNA fragment [P], which codes for protein P, with a DNA fragment [L], which codes for a flexible linker peptide L, and with a DNA fragment [R], which codes for a reporter protein R, forming thereby a fusion DNA fragment selected from the group consisting of [P-L-R] and [R-L-P], such that detection of R in the fusion proteins expressed by said [P-L-R] or [R-L-P] correlates with solubility of protein P;
   b. expressing the fusion DNA fragments [P-L-R] or [R-L-P] such that fusion proteins P-L-R or R-L-P are produced; and
   c. detecting the reporter protein R in the fusion protein P-L-R or R-L-P,
   wherein the reporter protein R is green fluorescent protein (GFP).

3. The method of claim 2, wherein the peptide linker L is chosen to be short, flexible, hydrophilic and soluble.

4. The method of claim 1, wherein said protein P is a fragment of a larger protein and said DNA fragment [P] is a fragment of a DNA which codes for said larger protein.

5. The method of claim 4, wherein said DNA fragment [P] is generated using methods selected from the group consisting of partial DNAse digest, radiation-induced fragmentation, chemical fragmentation, enzymatic digest, endonuclease digest, exonuclease digest, and acoustic/mechanical shearing.

6. The method of claim 5, wherein said DNA fragment [P] is size selected before fusing said DNA fragment [P] with DNA fragment [R], using methods selected from the group consisting of polyacrylamide gel electrophoresis, agarose gel electrophoresis, capillary electrophoresis, and high pressure liquid chromatography.

7. The method of claim 1, wherein the step of expressing the fusion DNA fragment is performed in vitro or in vivo.

* * * * *